(12) United States Patent
Schmidt et al.

(10) Patent No.: US 6,561,187 B2
(45) Date of Patent: *May 13, 2003

(54) CONTROL OF SUPPLEMENTAL RESPIRATORY OXYGEN

(75) Inventors: Matthew F. Schmidt, Lino Lakes, MN (US); John S. Buan, Maple Grove, MN (US); Catherine A. Nordman, St. Paul, MN (US)

(73) Assignee: Minnesota Innovative Technologies & Instruments Corporation, Lino Lakes, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/076,001

(22) Filed: Feb. 14, 2002

(65) Prior Publication Data

US 2002/0112726 A1 Aug. 22, 2002

Related U.S. Application Data

(63) Continuation of application No. 09/463,614, filed as application No. PCT/US98/15490 on Jul. 24, 1998, now Pat. No. 6,371,114, which is a continuation-in-part of application No. 08/900,686, filed on Jul. 25, 1997.
(60) Provisional application No. 60/064,578, filed on Nov. 4, 1997.

(51) Int. Cl.[7] ............................................. A61M 16/00
(52) U.S. Cl. .............................. 128/204.23; 128/204.18
(58) Field of Search ....................... 128/204.18, 204.21, 128/204.23, 204.26, 205.11, 205.23, 207.18; 600/323

(56) References Cited

U.S. PATENT DOCUMENTS

| | | | |
|---|---|---|---|
| 2,414,747 A | 1/1947 | Kirschbaum | |
| 2,912,979 A | 11/1959 | Lieber | |
| 3,400,712 A | 9/1968 | Finan | |
| 3,400,713 A | 9/1968 | Finan | |

(List continued on next page.)

FOREIGN PATENT DOCUMENTS

| | | |
|---|---|---|
| DE | 4309923 A1 | 9/1994 |
| EP | 0 099 283 A1 | 6/1983 |
| EP | 0 606 687 A2 | 12/1993 |
| WO | WO 99/04841 | 2/1999 |

OTHER PUBLICATIONS

Auerbach, D. et al., "An New Oxygen Canola System Using Intermittent–Demand Nasal Flow", *Chest*, 74, pp. 39–43 (1978).

(List continued on next page.)

*Primary Examiner*—Aaron J. Lewis
*Assistant Examiner*—Teena Mitchell
(74) *Attorney, Agent, or Firm*—Mueting, Raasch & Gebhardt, P.A.

(57) ABSTRACT

Methods and systems for supplying supplemental oxygen to patients for use in sub-acute care which maintains healthy blood oxygen content in the patients by controlled dosing of oxygen with a measured response to the patient's actual blood oxygen content are disclosed. The dosing can be provided by simple ON/OFF control over the delivery of oxygen or the amount of oxygen delivered to the patient with each inhalation can be varied in response to the patient's need as determined by a more sophisticated control scheme, such as a PID loop control algorithm, that utilizes the difference between the patient's actual blood oxygen content and a target blood oxygen content and/or trends in the blood oxygen content. The systems and methods are particularly directed at patients receiving supplemental oxygen in a sub-acute care environment.

21 Claims, 5 Drawing Sheets

U.S. PATENT DOCUMENTS

| | | |
|---|---|---|
| 3,493,703 A | 2/1970 | Finan |
| 3,734,091 A | 5/1973 | Taplin |
| 3,834,383 A | 9/1974 | Weigl et al. |
| 4,054,133 A | 10/1977 | Myers |
| 4,278,110 A | 7/1981 | Price et al. |
| 4,326,513 A | 4/1982 | Schulz et al. |
| 4,381,002 A | 4/1983 | Mon |
| 4,457,303 A | 7/1984 | Durkan |
| 4,461,293 A | 7/1984 | Chen |
| 4,462,398 A | 7/1984 | Durkan et al. |
| 4,484,578 A | 11/1984 | Durkan |
| 4,506,666 A | 3/1985 | Durkan |
| 4,519,387 A | 5/1985 | Durkan et al. |
| 4,567,888 A | 2/1986 | Robert et al. |
| 4,575,042 A | 3/1986 | Grimland et al. |
| 4,584,996 A | 4/1986 | Blum |
| 4,612,928 A | 9/1986 | Tiep et al. |
| 4,648,395 A | 3/1987 | Sato et al. |
| 4,665,911 A | 5/1987 | Williams et al. |
| 4,681,099 A | 7/1987 | Sato et al. |
| 4,686,974 A | 8/1987 | Sato et al. |
| 4,686,975 A | 8/1987 | Naimon et al. |
| 4,705,034 A | 11/1987 | Perkins |
| 4,706,664 A | 11/1987 | Snook et al. |
| 4,744,356 A | 5/1988 | Greenwood |
| 4,745,925 A | 5/1988 | Dietz |
| 4,784,130 A | 11/1988 | Kenyon et al. |
| 4,823,788 A | 4/1989 | Smith et al. |
| 4,827,922 A | 5/1989 | Champain et al. |
| 4,873,971 A | 10/1989 | Perkins |
| 4,889,116 A | 12/1989 | Taube |
| 4,932,402 A | 6/1990 | Snook et al. |
| 4,971,049 A | 11/1990 | Rotariu et al. |
| 5,005,570 A | 4/1991 | Perkins |
| 5,024,219 A | 6/1991 | Dietz |
| 5,038,770 A | 8/1991 | Perkins |
| 5,038,771 A | 8/1991 | Dietz |
| 5,048,515 A | 9/1991 | Sanso |
| 5,052,400 A | 10/1991 | Dietz |
| 5,074,299 A | 12/1991 | Dietz |
| 5,099,837 A | 3/1992 | Russel, Sr. et al. |
| 5,103,814 A * | 4/1992 | Maher .................. 128/204.18 |
| 5,137,017 A | 8/1992 | Salter |
| 5,165,397 A | 11/1992 | Arp |
| 5,251,632 A | 10/1993 | Delpy |
| 5,280,780 A | 1/1994 | Abel |
| 5,282,464 A | 2/1994 | Brain |
| 5,315,990 A | 5/1994 | Mondry |
| 5,323,776 A | 6/1994 | Blakeley et al. |
| 5,360,000 A | 11/1994 | Carter |
| 5,365,922 A * | 11/1994 | Raemer ................. 128/202.22 |
| 5,388,575 A | 2/1995 | Taube |
| 5,398,676 A * | 3/1995 | Press et al. ............ 128/204.18 |
| 5,398,682 A | 3/1995 | Lynn |
| 5,443,062 A | 8/1995 | Hayes |
| 5,495,848 A | 3/1996 | Aylsworth et al. |
| 5,546,933 A | 8/1996 | Rapoport et al. |
| 5,558,086 A * | 9/1996 | Smith et al. ........... 128/204.23 |
| 5,582,164 A | 12/1996 | Sanders |
| 5,603,315 A | 2/1997 | Sasso, Jr. |
| 5,626,131 A | 5/1997 | Chua et al. |
| 5,692,497 A * | 12/1997 | Schnitzer et al. ...... 128/204.18 |
| 5,697,364 A | 12/1997 | Chua et al. |
| 5,735,268 A | 4/1998 | Chua et al. |
| 5,752,509 A | 5/1998 | Lachmann et al. |
| 5,803,066 A * | 9/1998 | Rapoport et al. ...... 128/204.21 |
| 5,810,759 A | 9/1998 | Merz |
| 5,865,174 A | 2/1999 | Kloeppel |
| 5,915,381 A | 6/1999 | Nord |
| 5,925,831 A * | 7/1999 | Storsved ............... 128/204.23 |
| 5,927,274 A * | 7/1999 | Servidio et al. ....... 128/204.18 |
| 5,931,162 A * | 8/1999 | Christian ............... 128/204.18 |
| 5,937,853 A * | 8/1999 | Strom ................... 128/204.18 |
| 6,099,481 A | 8/2000 | Daniels et al. |
| 6,142,149 A * | 11/2000 | Steen .................... 128/204.21 |
| 6,152,134 A * | 11/2000 | Webber et al. ......... 128/204.18 |
| 6,186,142 B1 * | 2/2001 | Schmidt et al. ........ 128/204.23 |
| 6,192,883 B1 | 2/2001 | Miller, Jr. |
| 6,220,244 B1 | 4/2001 | McLaughlin |

OTHER PUBLICATIONS

Azhar, N., et al., "Automatic Feedback Control of Oxygen Therapy Using Pulse Oximetry", *Annual International Conference of the IEEE Engineering in Medicine and biology Society, 13* pp. 1614–1615.

Beddis, et al., "New Technique for Servo–Control of Arterial Oxygen Tension in Preterm Infants", *Archives of Diseases in Childhood, 54*, pp. 278–280 (1979).

Bhutani, V.K. et al., "Adaptive Control of Inspired Oxygen Delivery to the Neonate", *Pediatric Pulmonology, 14*, pp. 110–117 (1992).

Braun, S.R., et al., "Comparison of Six Oxygen Delivery Systems for COPD Pateitnts at Rest and During Exercise", *Chest*, 102, pp. 694–698 (1992).

Celli, B., et al., "Standards for the Diagnosis and Care of Patients with Chronic Obstructive Pulmonary Disease", *America J. Respir and Crit Care Medicine, 152*, pp. 77–120 (1995).

Collins, P., et al., "Apparatus for the Servocontrol of Arterial Oxygen Tension in Preterm Infants", *Med., & Biol. Eng. & Comput., 17*, pp. 449–453 (1979).

"Continuous of Nocturnal Oxygen Therapy in Hypoxemic Chronic Obstructive Lung Disease", *Annals of Internal Medicine, 93*, pp. 391–398 (1980).

Cotes, J.E., "Continuous Versus Intermittent Administration of Oxygen During Exercise to Patients with Chronic Lung Disease", *The Lancet*, pp. 1075–1077 (1963).

Decker, M.J. et al., "Extended Monitoring of Oxygen Saturation in Chronic Lung Disease", *Chest, 102*, pp. 1075–1079 (1992).

Make, B., "Oxygen Therapy", Jewish Center for Immunology And Respiratory Medicine, *Medical/Scientific Update, 11*, (1993).

Mecikalski, M., et al. "A Demand Valve Conserves Oxygen in Subjects with Chronic Obstructive Pulmonary Disease," *Chest, 86*, pp. 667–670 (1984).

Morozoff, P.E., et al. "Automatic Control of Blood Oxygen Saturation in Premature Infants", *Second IEEE Conference on Control Applications*, pp. 415–419 (1993).

Morozoff, P.E. et al., "Closed–loop Control of $SaO_2$ in the Neonate", *Biomedical Instrumentation and Technology, 26*, pp. 117–123 (1992).

Moyle, J.T.B., "Pulse Oximetry" (BMJ Publishing Group, London), pp. vii, ix, 1–134 (1994).

Raemer et al., D.B. "$Fl_x$ Controller: An Instrument to Automatically Adjust Inspired Oxygen Fraction Using Feedback Control From a Pulse Oximeter", *Journal of Clinical Monitoring, 13*, pp. 91–101 (1997).

Ritchie, G. et al. "Closed–Loop Control of Oxygen Delivery During Aeromedical Evacuation of Patient", *Proceeding of the IEEE Southeast Conference*, pp. 763–767 (1992).

Sano, A. et al., Adaptive Control of Arterial Oxygen Pressure of Newborn Infants Under Incubator Oxygen Treatments, *IEEE Proceedings, 132*, pp. 205–211 (1985).

Sliwinski, P. et al., "The adequacy of oxygenation of oxygenation in COPD patients undergoing long–term oxygen therapy assessed by pulse oximetry at home", *European Respiratory Journal 7*, pp. 274–278 (1994).

Smith, R., "Carrying On: Portable Oxygen stands out as a value–added service to referral sources", *Home Health Care Dealer/Supplier*, pp. 43–44, 46 (1997).

Tehrani et al. "An Automatic Control System for Oxygen Therapy of Newborn Infants", *Annual International Conference of the IEEE Engineering in Medicine and Biology Society, 13*, pp. 2180–2182 (1991).

Tehrani et al."A Feedback Controller for Supplemental Oxygen Treatment of Newborn Infants: A Simulation Study", *Med. Eng. Phys., 16*, pp. 329–333 (1994).

Tiep, B.L. et al., "Low–concentration Oxygen Therapy Via a Demand Oxygen Delivery System", *Chest, 87*, pp. 636–638 (1985).

Tiep, B.L. et al., "Future Direction for Long–Term Oxygen Therapy", *Lung Biology in Health and Disease*, pp. 347–362.

Weill, D. et al.. "Oxygen–Conserving Devices" *Lund Biology in Health and Disease, 81*, pp. 235–256 (1995).

Weitzner, S.W. et al., "The Rate of Arterial Oxygen Desaturation During Apnea in Humans", *Anesthesiology,20*, pp. 624–627 (1959).

Yu, C. et al. "Improvement in Arterial Oxygen Control Using Multiple–Model Adaptive Control Procedures", *IEEE Transactions on Biomedical Engineering, BME–34*, pp. 567–574 (1987).

* cited by examiner

CONTROL OF SUPPLEMENTAL RESPIRATORY OXYGEN

This is a continuation of application Ser. No. 09/463,614, filed May 8, 2000, (6,371,114), which is a U.S. National Stage application of PCT/US98/15490, filed Jul. 24, 1998 which is a continuation-in-part of application Ser. No. 08/900,686, filed Jul. 25, 1997 (pending) which claims the benefit of Provisional application Ser. No. 09/084,578, filed Nov. 4, 1997, which are all incorporated herein by reference.

The present invention relates to the field of supplemental respiratory oxygen supply systems and methods. More particularly, the present invention provides methods and systems that conserve supplemental respiratory oxygen.

BACKGROUND

A large patient community is currently undergoing oxygen therapy at home or in long-term care facilities, such as nursing homes. Supplemental respiratory oxygen has been a widely accepted form of treatment for COPD (chronic obstructive pulmonary disease) patients with hypoxemia following the completion of a major National Institutes of Health study in 1980. The Nocturnal Oxygen Therapy Trial established the efficacy of continuous oxygen therapy in the extension of the life span of sufferers of COPD with chronic hypoxemia.

For administration of long-term oxygen therapy it has been common practice to deliver the oxygen directly into the nostrils of the patient through a device known as a nasal cannula. The cannula is connected via a supply hose to a source of oxygen, such as an oxygen concentrator, liquid oxygen dewar or high pressure gas cylinder. The oxygen is delivered continuously to the patient at a rate prescribed by a physician.

It has been recognized that continuous oxygen delivery is wasteful of oxygen, as a patient needs oxygen only when they are inhaling and the oxygen delivered at other times is wasted. The most significant financial cost associated with this waste is found in the increased service visits required by the oxygen provider to replenish the patient's oxygen supply, because the actual cost of the oxygen is only a small fraction of the total cost of the therapy.

Another problem associated with supplemental oxygen therapy is that the physical size and weight of the oxygen apparatus can reduce the patient's mobility.

A number of approaches have been taken to address the problems of waste, cost and portability of oxygen therapy. The therapeutic approach that has grown out of this body of work is typically referred to as "demand delivery." The devices respond to a patient's inspiratory effort by delivering a predetermined pulse of oxygen during the period of inhalation, rather than allow the oxygen to flow to the patient continuously. There are many ways in which this basic concept has been implemented.

Extensive work has been done on sensors, timing of oxygen release, and algorithms for delivery of the oxygen. A variety of methods for sensing the respiratory cycle have been used, including pressure sensors that are in fluidic communication with the patient's airway, flow sensors, and chest belts which detect the movement of the thorax during respiration. Some systems deliver a small bolus of oxygen at the beginning of inhalation, while others deliver continuous flow throughout inhalation. There has also been work on the frequency of delivery. For example, some systems do not provide oxygen at every breath.

In spite of the large variety of approaches taken to conserve oxygen supplies and/or reduce the size and weight of the oxygen supply equipment, no consensus has yet been reached as to the most appropriate way to save oxygen and medicate the patient adequately.

The simplest approaches to conserve oxygen involve detection of inhalation as a trigger to deliver oxygen. A variety of detection devices were developed in pursuit of this basic approach to controlling oxygen supply, including a chest belt worn by the patient that generates an electrical signal to trigger the opening of the oxygen supply valve; a hand-activated breathing device attached to a portable gas bottle via a supply hose in which users would dispense the oxygen by pushing a button while holding the device next to their mouth; a mechanical chest strap/valve that functions as both an inhalation sensor and delivery device in an oxygen conserving system; and an all-pneumatic, fluidically-controlled device.

Another approach uses pressure sensors in the oxygen line to monitor line pressure at the nostrils. A small negative pressure, indicative of the onset of inhalation, triggers the release of oxygen. This type of detection scheme has become the standard method and is employed by most systems currently in use. The systems attempt to provide a physiologically equivalent dose of oxygen, when compared to continuous flow, by providing a burst of oxygen at the onset of inhalation. By providing more oxygen at the beginning of inhalation, when it is more physiologically useful, the most efficient of these systems claim to be able to reduce oxygen consumption.

The existing demand delivery devices provide economic benefit in the form of oxygen savings (and reduced service visits), but it is often at the expense of the level of medical care. In particular, some patients have been found to have deficient levels of oxygen in their blood as a result of using known demand delivery devices. Certain activities, such as exercise and sleep, cause the body's need for oxygen to fluctuate in an unpredictable manner. The chronic hypoxemia being corrected by the prescription of oxygen therapy is not fully ameliorated by these devices.

Because demand delivery devices and continuous flow systems do not measure the patient's blood oxygen saturation, they do not respond to a change in patient need as would be indicated by a drop in oxygen saturation. The oxygen flow in the form of pulses of gas is fixed in some devices, such as the PulseDose by DeVilbiss, as it is delivered with every breath. In other devices, such as the Oxymatic 301 from Chad Therapeutics, the patient is allowed some adjustability in the flow by determining the frequency of pulses as a function of the number of breaths; i.e., one pulse every fourth breath, a pulse every other breath, etc. None of these types of demand delivery system is capable of directly addressing fluctuations in the blood oxygen level experienced by the user.

In fact, while it is generally known that existing modes of oxygen therapy are inadequate for most patients at least some of the time (that is, acute periods of hypoxia, $SaO_2 < 88\%$, can be seen in virtually all patients for some fraction of each day), another problem that is not addressed by the known devices and methods is that the average COPD patient is receiving more oxygen than needed for a significant part of each day. For example, the oxygen patients studied by Decker, et al. (Chest 1992) had an $SaO_2$ greater than 90% for more than 70% of the time they spent breathing room air without any supplemental oxygen. In another study of even sicker patients (Sliwinski, et al., European Respiratory Journal 1994), $SaO_2$ was greater than 88% for 40% of the time while breathing room air, and greater than 92%

(higher than necessary) for about 70% of the time they were using their supplemental oxygen. The lack of methods and/or systems for controlling the upper limit of blood oxygen content results in significant amounts of wasted oxygen.

Devices which control the flow of oxygen based on blood oxygen measurements from various types of sensors have been described for a variety of applications. However, none of these devices were meant for residential use by sub-acute COPD patients, none had the goal or object of conserving as much oxygen as possible while still maintaining a healthy blood oxygen level, and none used a pulsed, demand-delivery method for conserving oxygen.

Measurements of blood oxygen saturation can be broken into two groups of measurement strategies: invasive and non-invasive. An invasive measurement using existing technology requires that blood be drawn from the body and the sample placed in a blood gas analyzer. One common non-invasive blood oxygen sensor is a pulse oximeter which relies on the differences in the light absorption curves of saturated and desaturated hemoglobin in the infrared and near-infrared portions of the spectrum. The typical pulse oximeter sensor includes two LED's, one red and one infrared. As the light from the two LED's passes through a capillary bed at the point of attachment, such as is found on the finger, the light is partially absorbed by the blood and tissues and then is detected by a photodetector. The electrical signal generated by the photodetector, which is proportional to the amount of light absorbed by the body, is transmitted to the oximeter. The absorption measurements can be made rapidly, up to 500 times per second for each LED. Because of the pulsatile nature of arterial blood, the absorption as a function of time will vary slightly at the frequency of the pulse. This allows the oximeter to extract the arterial blood oxygen saturation information from background noise caused by absorption in tissues located between the LED's and the photodetector. Pulse oximetry is a well-accepted technique and can be found in machines used for monitoring patients under anesthesia, patients participating in sleep studies and neonatal monitoring.

Some methods and systems for controlling oxygen delivery to patients in critical care settings have been disclosed. Some of the systems use feedback loop controllers that use the blood oxygen saturation signal, $SpO_2$, from a pulse oximeter to control the inspired oxygen fraction ($FIO_2$) in the respiratory gas delivered by a mechanical ventilator in which oxygen is mixed with air to supply an accurate amount of oxygen to a patient through a mask or hood. These systems are intended for the care of critically ill patients receiving treatment in hospitals for severe respiratory distress caused by a chronic condition or accident.

SUMMARY OF THE INVENTION

The present invention provides supplemental respiratory oxygen supply methods and systems which maintain healthy blood oxygen saturation in sub-acute patients receiving supplemental oxygen by controlling the dosing of oxygen with a measured response to the patient's actual blood oxygen saturation levels. This closed-loop control of oxygen flow for COPD patients provides for both healthy blood oxygen levels and significant oxygen conservation by reducing or preventing the delivery of supplemental respiratory oxygen during those times when the patient has a desired blood oxygen level.

In one aspect, the present invention provides a method of controlling supplemental oxygen delivery during sub-acute care by continuously measuring blood oxygen content of a patient to obtain a measured blood oxygen content level; delivering supplemental oxygen from an oxygen source to the patient when the patient is inhaling if the measured blood oxygen content level is below a desired value; and restricting the delivery of supplemental oxygen if the measured blood oxygen content level of the patient is above the desired value.

In another aspect, the present invention provides a method of controlling supplemental oxygen delivery for sub-acute care by continuously measuring blood oxygen content of a patient to obtain a measured blood oxygen content level; sensing variations in respiration of the patient to determine when the patient is inhaling; delivering supplemental oxygen from an oxygen source to the patient through a supplemental oxygen delivery device when the patient is inhaling if the measured blood oxygen content level is below a desired value; and restricting the delivery of supplemental oxygen to the patient through the supplemental oxygen delivery device if the measured blood oxygen content level of the patient is above the desired value.

In another aspect, the present invention provides a method of controlling supplemental oxygen delivery for sub-acute care by continuously measuring blood oxygen content of a patient to obtain a measured blood oxygen content level; delivering a variable dose of supplemental oxygen from an oxygen source to the patient when the patient is inhaling, wherein the variable dose is at least partially determined based on the measured blood oxygen content level.

In another aspect, the present invention provides a method of controlling supplemental oxygen delivery for sub-acute care by continuously measuring blood oxygen content of a patient to obtain a measured blood oxygen content level; sensing variations in respiration of the patient to determine when the patient is inhaling; delivering a variable dose of supplemental oxygen from an oxygen source to the patient through a supplemental oxygen delivery device when the patient is inhaling, wherein the variable dose of supplemental oxygen is at least partially based on a difference between the desired value for the measured blood oxygen content level and the measured blood oxygen content level.

In another aspect, the present invention provides a method of sensing variations in respiration of a patient by providing a flow sensor in fluid communication with the respiratory flow of a patient; monitoring the flow sensor to determine when the patient is inspiring air; and monitoring the flow sensor to determine when the patient is expiring air.

In another aspect, the present invention provides a demand delivery method for controlling the delivery of oxygen to a patient by providing a flow sensor in fluid communication with the respiratory flow of a patient; monitoring the flow sensor to determine when the patient is inhaling; delivering oxygen to the patient when the patient is inhaling; monitoring the flow sensor to determine when the patient is exhaling; restricting delivery of oxygen to the patient when the patient is exhaling.

In another aspect, the present invention provides a system for delivering supplemental oxygen for sub-acute care, the system including a blood oxygen content level sensor; a source of supplemental oxygen; a valve in fluid communication with the source of supplemental oxygen; and a controller capable of operating the valve, the controller restricting flow through the valve when the blood oxygen content level measured by the blood oxygen content level sensor is above a desired value.

In another aspect, the present invention provides a system for controlling supplemental oxygen delivery including means for measuring blood oxygen content level of a patient; means for delivering supplemental oxygen from an oxygen source to the patient when the patient is inhaling if the measured blood oxygen content level is below a desired level; and means for restricting the delivery of supplemental oxygen from the oxygen source to the patient if the measured blood oxygen content of the patient is above a desired level.

In another aspect, the present invention provides a system for controlling supplemental oxygen delivery including means for measuring blood oxygen content level of a patient; and means for delivering a variable dose of supplemental oxygen from an oxygen source to the patient when the patient is inhaling, wherein the variable dose is at least partially determined based on the measured blood oxygen content.

As used in connection with the present invention, the terms "supplemental oxygen" and "supplemental respiratory oxygen" refer to oxygen delivered to patients in addition to the oxygen received by the patient through the inspiration of room or ambient air. Because room air contains some oxygen, the supplemental oxygen is provided in addition to the oxygen that would normally be inspired by the patient.

As used in connection with the present invention, the term "blood oxygen content" and "blood oxygen content level" will typically be used to refer to blood oxygen saturation as commonly measured by the percentage of oxygen-saturated hemoglobin ($SpO_2$) although it can also refer to any suitable measurement for determining the level of oxygenation in a patient's blood. For example, it will be understood that blood oxygen content can also be obtained based on data from a CO-oximeter. Furthermore, blood oxygen content, can also be obtained based on partial pressures of oxygen ($PaO_2$).

As used in connection with the present invention, the term "sub-acute care" refers to care provided to patients that is not intended to treat critical conditions. Typically, sub-acute care is provided to patients in residential settings. "Residential" preferably includes, e.g., homes and long-term care facilities (such as nursing homes). Sub-acute care also includes care delivered in ambulatory situations, i.e., when the patient is engaged in normal activities outside of his or her residence, such as shopping, attending concerts or other events, traveling to appointments with health care professionals, etc.

As used in connection with the present invention, the terms "continuous" and "continuously" (when referring to the measuring of blood oxygen content levels) mean that the blood oxygen content level of the patient will be measured without cessation or at intervals (fixed or variable) that are sufficiently small to provide the advantages of the invention.

These and other features and advantages of the present invention will be apparent upon review of the detailed description of the invention and accompanying drawings.

DETAILED DESCRIPTION OF ILLUSTRATIVE EMBODIMENTS OF THE INVENTION

Figure 1:
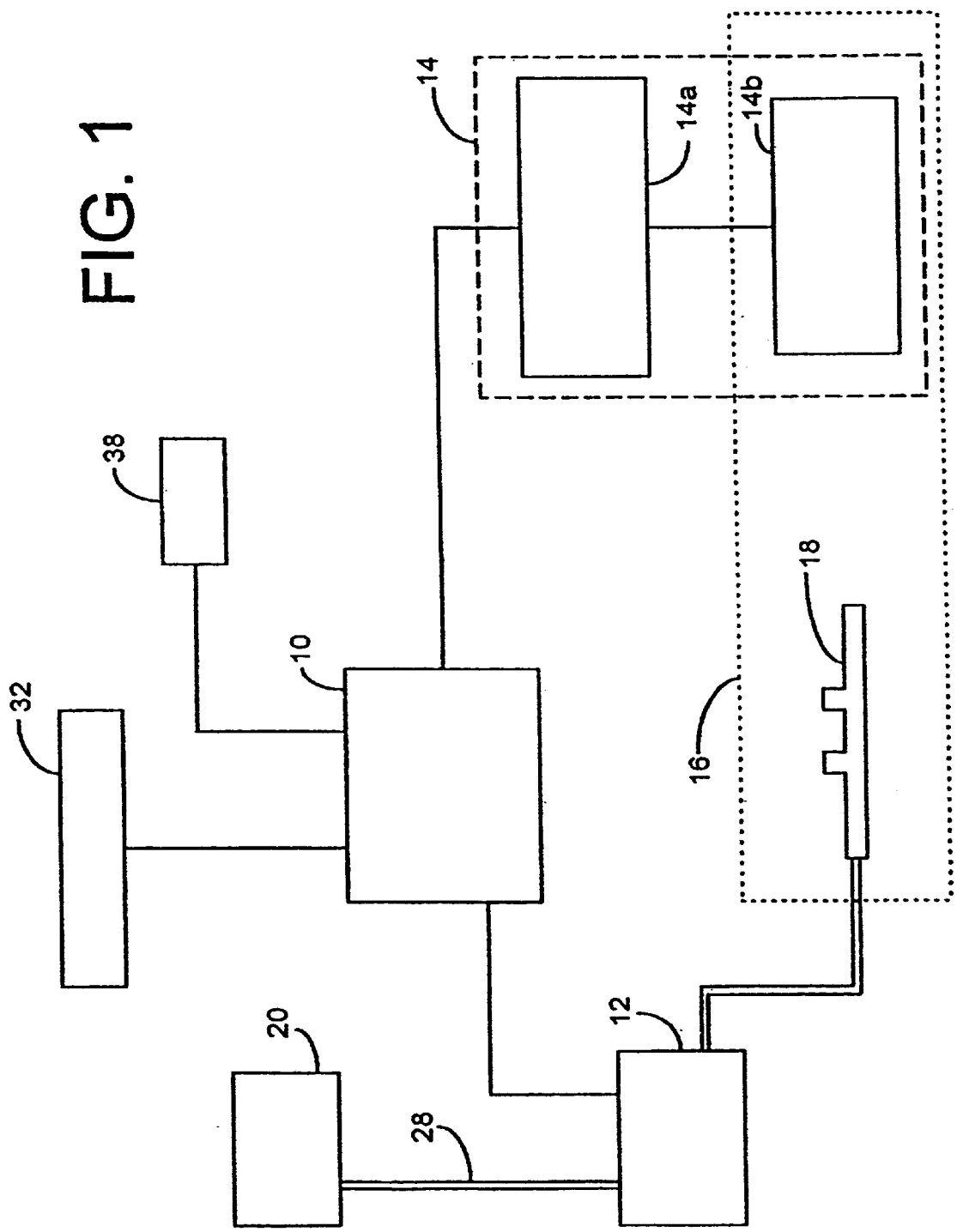
FIG. 1 is a block diagram of one system according to the present invention.

As described above, the present invention provides demand respirating oxygen supply methods and apparatus for use in sub-acute care which maintain healthy blood oxygen saturation in patients by controlled dosing of oxygen with a measured response to the patient's actual blood oxygen content. The dosing can be provided by simple on/off control over the delivery of oxygen or the amount of oxygen delivered to the patient with each inhalation can be varied in response to the patient's need as determined by a more sophisticated control scheme, such as a proportional-integral-derivative (PID) loop control algorithm, that utilizes the difference between the patient's measured blood oxygen content level and a desired or target blood oxygen content level.

The systems and methods of the present invention are particularly directed at patients receiving supplemental oxygen in a sub-acute care environment, more preferably in a residential setting. The needs and considerations of patients receiving supplemental oxygen in sub-acute care differ from those present when providing oxygen to patients in critical care environments, in which the amounts of oxygen delivered to patients are carefully controlled in connection with masks or other enclosures that do not typically allow the patents to inspire room air in uncontrolled manners. In those situations, the fractional amount of inspired oxygen ($FIO_2$) is typically controlled by mixing oxygen and air in a blender or other device before delivering the gas to the patient.

Among the advantages of the present invention are the significant conservation of oxygen provided by delivering only the amount of oxygen needed to maintain a healthy blood oxygen content and the ability to address therapeutic problems associated with demand delivery systems by providing the correct amount of oxygen to the patient to reduce uncontrolled hypoxic events.

The amounts of oxygen that can be conserved by implementing the methods according to the present invention can be significant, even compared to known demand delivery systems that conserve oxygen by simply turning the supply on or off during a patient's respiration. Studies have reported oxygen savings ratios of from 3:1 to 7:1 for known simple demand delivery systems. In other words, a fixed amount of oxygen can last three to seven times as long as the same amount of oxygen would last in a supplemental oxygen delivery system that does not include a simple demand delivery system. Implementation of the methods according to the present invention by using a demand delivery approach with a feedback control mechanism that responds to a continuous blood oxygenation measurement could provide an oxygen savings ratio of greater than 13:1 while maintaining the patient's $SaO_2$ at the 90% level.

Other advantages of the methods and apparatus according to the present invention are the ability to integrate the invention with any sub-acute care supplemental oxygen supply system, including both ambulatory and stationary sources. For unlimited volume sources, such as oxygen concentrators and membrane separators, the invention will reduce their size and energy consumption for a given level of therapy. For fixed volume gas sources, such as liquid and high pressure gas, the invention will extend the lifetime of the oxygen supply, thereby significantly decreasing the cost of providing that treatment.

If the system is ambulatory, the present invention can allow for reductions in the size and weight of the oxygen source, thereby increasing the patient's mobility. An added benefit of reducing the size and/or weight of the ambulatory systems is the potential for a better therapeutic outcome. If patients find the smaller, lighter weight systems less cosmetically unattractive they will be more likely to carry and use the systems during ambulatory activities as opposed to not using the systems. Studies have shown that the benefit of supplemental oxygen systems is significantly reduced if the systems are not used on a regular basis.

Another advantage of the invention, method and apparatus, is a reduction in the risk of hypercapnia (carbon dioxide retention) by only providing enough oxygen to reach a predetermined blood oxygen saturation, typically about 90% as measured by a conventional two-color pulse oximeter.

One embodiment of an automated respiratory oxygen supply system is depicted in FIG. 1 and includes a controller 10, a demand delivery module 12, and a blood oxygen content sensor 14 connected to the patient 16. Oxygen is supplied from an oxygen source 20 to the patient 16 by the demand delivery module 12 through, in the preferred embodiments, a supplemental oxygen delivery device 18. The preferred system may also include a user interface 32 and an alarm 38.

The supplemental oxygen delivery device 18 is preferably a nasal cannula as depicted in FIG. 1, although it will be understood that the supplemental oxygen delivery device can take the form of any device designed to provide supplemental respiratory oxygen to a patient while not preventing the patient from also inspiring room or ambient air in addition to the supplemental respiratory oxygen from an oxygen source. Examples of other supplemental oxygen delivery devices include, but are not limited to: tracheal catheters, nasal masks designed for use with Continuous Positive Airway Pressure (CPAP) systems, vented masks that cover both the nose and the mouth but that allow inspiration of room air in uncontrolled amounts in addition to the supplemental oxygen delivered to the mask, etc.

Oxygen source 20 could be an oxygen concentrator, membrane separator, high pressure cylinder or liquid oxygen dewar. This could also include any portable versions of oxygen sources 20. Other potential sources of oxygen gas suitable for providing supplemental oxygen in sub-acute care in a residential setting and/ambulatory situations may be created in the future and should be considered as being functional with the described invention. As used below, "line" will refer to any connection made between the oxygen source, the described invention and the patient.

If the oxygen source 20 is an oxygen concentrator, typically a continuous low-flow device, usually delivering at most 6 liters/min of 96% oxygen, the system may also include an oxygen storage device to accommodate the periodic higher flows that are necessary to practice the methods described below. If high flow concentrators become available, such a storage device would not be needed.

One controller 10 is an electronic circuit including a software programmable microcontroller as its main component. Depending on the allocation of tasks within the device a number of microcontrollers could be used as a controller 10. In one embodiment, the controller 10 includes a serial data input port, A/D converter, LED driver capabilities and digital I/O pins. One example of a suitable controller is the PIC 16C74A microcontroller from Microchip Technology Inc. of Chandler, Ariz.

Those skilled in the art will realize that a great deal of optimization may be done relative to the choice of a microcontroller(s). Specifications, such as power consumption, cost, memory size, clock speed and part availability may alter the choice for a preferred microcontroller. Furthermore, many of the functions described for the microcontroller in the preferred embodiment could be accomplished by using discrete circuits of many types. Additionally, the microcontroller and its peripheral circuitry may be replaced entirely by discrete circuitry, such as programmable logic arrays, A/D converter chips, analog comparators, etc.

The system also includes an oxygen content sensor 14 for monitoring the blood oxygen content of the patient 16. One suitable sensor 14 includes a sensor control module 14a and a sensor 14b typically mounted or attached to the patient 16 by some suitable technique. The information from the oxygen content sensor 14 is fed back to the controller 10 for use in executing the methods according to the present invention. It is preferred, but not required, that the oxygen sensor 14 provide a signal to the system controller 10 in the form of a blood oxygen saturation in percent. The sensor 14 preferably, but not necessarily, processes all of its data internally and the controller 10 preferably processes only error flags and numerical information as described shortly.

One preferred oxygen sensor 14 is a non-invasive sensor such as a two-color pulse oximeter. As used herein, the terms "pulse oximeter" or "oxygen sensor" will include both the optical sensor and the circuitry used to determine blood oxygen saturation levels using the optical sensor. One example of a suitable pulse oximeter is a conventional two-color, OEM-II oximeter module, from Nonin Medical Inc. of Plymouth, Minn., that can measure the percentage of oxygen-saturated hemoglobin, $SpO_2$, in the blood stream of an in vivo respiratory system. The preferred embodiment of the pulse oximeter 14 uses a transmitting sensor that attaches to the user's finger. Alternative embodiments may employ sensors that attach elsewhere on the body.

While the pulse oximeter is one preferred non-invasive oxygen sensor, it should be understood that any blood oxygen sensor, invasive or non-invasive, useful for determining blood oxygen content levels (preferably continuously) could be used in connection with the present invention. It should also be apparent to those skilled in the art that technologies on the horizon, such as an implantable, micro-electromechanical (MEMS) blood gas analyzer, may provide the blood oxygen content information needed by the system controller 10. Furthermore, there may be improvements in pulse oximetry technology, such as the ability to determine the level of carboxyhemoglobin in the blood, that may be useful for the described invention. Use of these new blood oxygen content technologies in oxygen conservers for long-term oxygen therapy should be considered to lie within the scope of the systems and methods of the present invention provided they have the ability to provide suitable blood oxygen content measurements.

In one embodiment, the pulse oximeter 14 deconvolves the optical information into a blood oxygen saturation value, $SpO_2$, in percent. The oximeter 14 outputs a serial data stream with this information to the controller 10 for evaluation. Other important information may also be included in the oximeter data stream, such as the user's pulse rate and error flags that detail the reliability of the $SpO_2$ and pulse rate values.

It will be recognized by those skilled in the art that an alternative embodiment may be provided in which the system controller 10 functions as the sensor control module 14a. As a result, data evaluation and error handling would be accomplished within the system controller 10 with an appropriate oxygen sensor 14b being attached to the patient 16.

Blood oxygen content measuring in connection with the present invention is described as "continuous" although it will be understood that the measurements made using, e.g., pulse oximeters and other devices, may actually be taken at discrete intervals. As discussed above, "continuous" as used in connection with the measuring of blood oxygen content in the present invention includes measurement of the blood oxygen content levels of the patient at intervals (fixed or variable) that are sufficiently small to provide the advantages of the invention. Preferably the sampling intervals will be less than about five minutes, more preferably less than about one minute, and even more preferably less than about one respiration interval (i.e., the time between the onset of two inhalations by the patient).

The information relating to blood oxygen content provided by the oxygen sensor 16 is then used by the system controller 10 in combination with the demand delivery module 12 to provide control over the oxygen supplied to the patient 16 from the oxygen source 20 as described in connection with the methods according to the present invention below.

Figure 2:
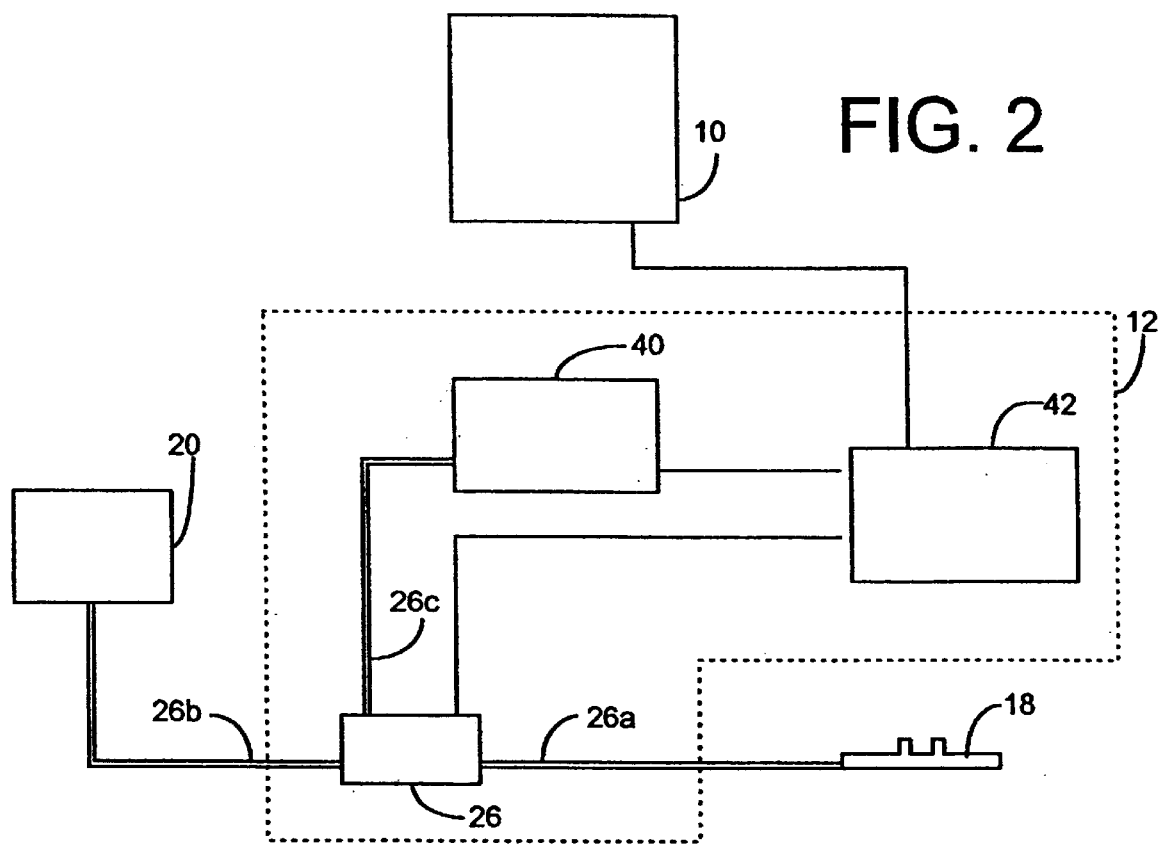
FIG. 2 is a block diagram of one demand delivery module for use in a system such as that depicted in FIG. 1.

A block diagram illustrating the components of one embodiment of a demand delivery module 12 according to the present invention is depicted in FIG. 2. One component in the demand delivery module 12 is an inhalation or respiration sensor 40 that monitors the respiratory activity of the patient 16 to determine variations in respiration of the patient. It is preferred that the variations in respiration allow the determination of when the patient is inhaling, although other portions of the respiratory cycle may actually be sensed. In other words, inhalation is preferably sensed, but in some cases it may be desirable to determine when inhalation is occurring based on the sensing of some other condition, activity, etc. such as chest movement, exhalation, etc.

In one embodiment, the respiration sensor 40 provides a signal to a respiration sensor/valve controller 42 that, in turn, controls the valve 26 based on additional input from system controller 10 (as will be described in more detail below).

The respiration sensor 40 can take a variety of forms that will be known to those skilled in the art. One type of suitable respiration sensor 40 monitors flow in the line used to supply oxygen to the supplemental oxygen delivery device 18. The sensor 40 in FIG. 2 monitors flow through the valve 26 interposed in the line between the supplemental oxygen delivery device 18 and the oxygen source 20. One suitable flow sensor is a Honeywell AWM2150 Microbridge Mass Airflow Sensor (available from Honeywell Corp., Minneapolis, Minn.).

Another feature of the preferred respiration sensor 40 is the ability to sense bidirectional flow, i.e., flow in each direction through the sensor 40. It is preferred that the flow generated by inhaling causes a voltage output of one polarity from the sensor 40, while flow generated by exhaling causes an output voltage of the opposite polarity. In any event, it is preferred that the sensor 40 be capable of detecting both inspiration and expiration.

In addition to the preferred flow sensor, it should be understood that other types of sensors may be utilized to detect variations in respiration, preferably inhalation and exhalation. Those skilled in the art will recognize that pressure transducers, thermistors or infrared detectors may all be used to sense inhalation. In one example, a pressure transducer with the appropriate sensitivity, such as a solid-state piezoresistive, capacitive or electromechanical device, could be used to generate an electrical signal in response to the breathing cycle. In another example, thermistors could be used to detect changes in airflow due to respiration. If the thermistor was sufficiently sensitive, one may be able to ascertain the onset of inhalation by monitoring the temperature of a thermistor (or thermocouple) placed near the nostril. A flow measurement may also be possible with the use of two thermistors in an anemometer configuration. Infrared detectors, such as single element bolometers, could be used as well if they possess the speed and accuracy to distinguish variations in respiration.

The respiration sensor 40 provides a signal to the respiration sensor/valve controller 42 which compares the signal to a predetermined reference level. The respiration sensor/valve controller 42 identifies the onset of inhalation by triggering when the sensor signal reaches the predetermined reference level. The respiration sensor/valve controller 42 then provides a signal to position the spool of valve 26 so oxygen flows from supply 20 to patient 16 via supplemental oxygen delivery device 18. The spool of the valve 26 remains in this position for a period of time, the "dose time" (D), as specified by the system controller 10. In this manner, a dose of oxygen of duration D can be provided when the patient is inhaling.

One preferred valve 26 of the embodiment of FIG. 2 is a three-way, two-position, solenoid-actuated spool valve having three ports 26a, 26b, 26c. Common port 26a is connected to the in vivo respiratory system of the patient 16 by the supplemental oxygen delivery device 18. Normally closed port 26b is connected to the oxygen source 20 and normally open port 26c is connected to respiration sensor 40 (with the other end of the preferred respiration sensor left open to atmosphere). One preferred valve 26 is manufactured by The Lee Company, of Westbrook, Conn., Model HDI LHDA0523111H.

When oxygen is not being supplied to the patient 16, the spool of the valve 26 is positioned such that common port 26a and normally open port 26c are connected so that the respiration sensor 40, supplemental oxygen delivery device 18, and patient 16 are in fluid communication, corresponding to the OFF position of the valve 26. This allows the respiratory effort of the patient 16 to be detected by the respiration sensor 40, through the monitoring of the flow generated in the supplemental oxygen delivery device 18 by inspiratory and expiratory efforts.

To supply oxygen to the patient 16, the spool of the valve 26 is moved so as to connect common port 26a and normally closed port 26b, corresponding to the ON position of the valve 26. This, in turn, allows for flow of respiratory oxygen to the patient 16 from supply 20 through the valve 26 and the supplemental oxygen delivery device 18.

The ON period for the valve 26, corresponding to the dosage period as discussed below, is preferably shorter than the inhalation period for the patient. As a result, the patient may often be inhaling after the valve 26 is OFF (i.e., closed). To reduce or prevent multiple openings of the valve 26 during a single inhalation, it is preferred that the valve 26 remain closed until the sensor 40 detects the onset of exhalation. Once exhalation is detected based on the sensor 40, the system can then resume monitoring for the onset of inhalation, whereupon the cycle is repeated.

Because the preferred valve 26 is a 3-port valve, there is a short period after opening or closing the valve 26, (the "bounce period") where the sensor output voltage spikes or bounces due to oxygen leaking from the normally closed port 26b to the normally open port 26c while the valve spool is still moving. Once the valve 26 is fully ON or OFF and the valve spool has stopped moving, the bounce signal disappears. It is preferred that monitoring of the respiration sensor 40 be adjusted to avoid false readings due to the bounce signal after turning the valve 26 ON or OFF. This adjustment can take the form of a delay in monitoring the signal provided by the sensor 40 after moving the valve 26 between the ON and OFF positions until the bounce signal has passed.

In some systems, the bounce signal may be monitored and used advantageously. The bounce signal (whether generated during ON or OFF movement of the valve spool) may be used to detect the presence of oxygen at the supply 20. No bounce signal may indicate that no oxygen is present because of the lack of pressurized oxygen at normally closed port 26b. In the preferred embodiment, the bounce signal generated by turning the valve 26 to the OFF position (i.e., closing port 26b) is used for this check because that bounce signal is typically larger and longer in duration than the bounce signal generated by turning the valve 26 to the ON position (i.e., opening port 26b).

Another advantage of the 3-port valve 26 is that sensor's zero-flow offset voltage can be checked while the valve 26 is in the ON position. The measured sensor offset voltage signal (Vo) can be used to generate a correction for drift in the sensor offset voltage. After the valve 26 has been ON longer than the valve-ON bounce period, the signal from the respiration sensor 40 can be read and recorded for use in, e.g., a software-generated correction for zero-flow sensor offset voltage. This sensor offset voltage signal is obtained from the respiration sensor 40 when the valve 26 is ON because no flow is to be expected through the respiration sensor 40 under those conditions (port 26c is closed). In addition, if this offset reading is greater (in absolute value) than a predefined upper limit (VoMAX), this can be used to indicate either sensor 40 or valve 26 failure; e.g., the sensor 40 has drifted too far out of specification, the valve 26 is leaking, the valve 26 is stuck in the OFF position, etc.

The demand delivery module 12 described above is a subsystem that communicates to and receives communication from system controller 10. In the described methods, it receives continually updated values of the dose time D. It will be understood, however, that those skilled in the art could design a demand delivery module 12 which is more or less dependent on the system controller 10 than is described in this embodiment. For example, it may be desirable to construct a system where respiration sensor 40 provides a signal directly to the system controller 10 with no separate respiration sensor/valve controller 42 being provided. The controller 10 would then provide a control signal to valve 26 directly as well as perform the other operations that are described as being performed by the respiration sensor/valve controller 42.

Moreover, it should be understood that alternative designs for the connections of the valve 26, respiration sensor 40, oxygen source 20, and patient 16 may be envisioned by the those skilled in the art. It would be possible to design a system in which an in-line flow sensor and/or three-port, two-way valve are not required. For example, the designs may involve a plurality of valves and sensors. It should be understood that the methods and systems of the described device operate independently from the specific configuration of hardware used for sensing variations in respiration and the specific valve configuration used to control the flow of oxygen.

Although the demand delivery module 12 described above is used to control delivery of supplemental oxygen to a patient from the source 20, the demand delivery module 12 and the methods of operating it as described above could find wider application. For example, they could be used in connection with critical care systems in which $FiO_2$ is to be controlled via the use of masks or other delivery devices used in connection with, e.g., respirators, ventilators, BIPAP (Bilevel Positive Airway Pressure) systems, etc. As a result, the demand delivery module and methods of operating it are not to be limited to use in connection with systems and methods of delivering supplemental oxygen as part of a sub-acute care regime.

As long as the data stream from the blood oxygen content sensor 14 is valid (as described in detail below), the controller 10 can use the data to control delivery of oxygen to the patient. The feedback control can be implemented as a portion of software code contained in the controller 10; however, it could alternatively be a hard-wired controller or combination of hardware and software in other embodiments.

Figure 3A:
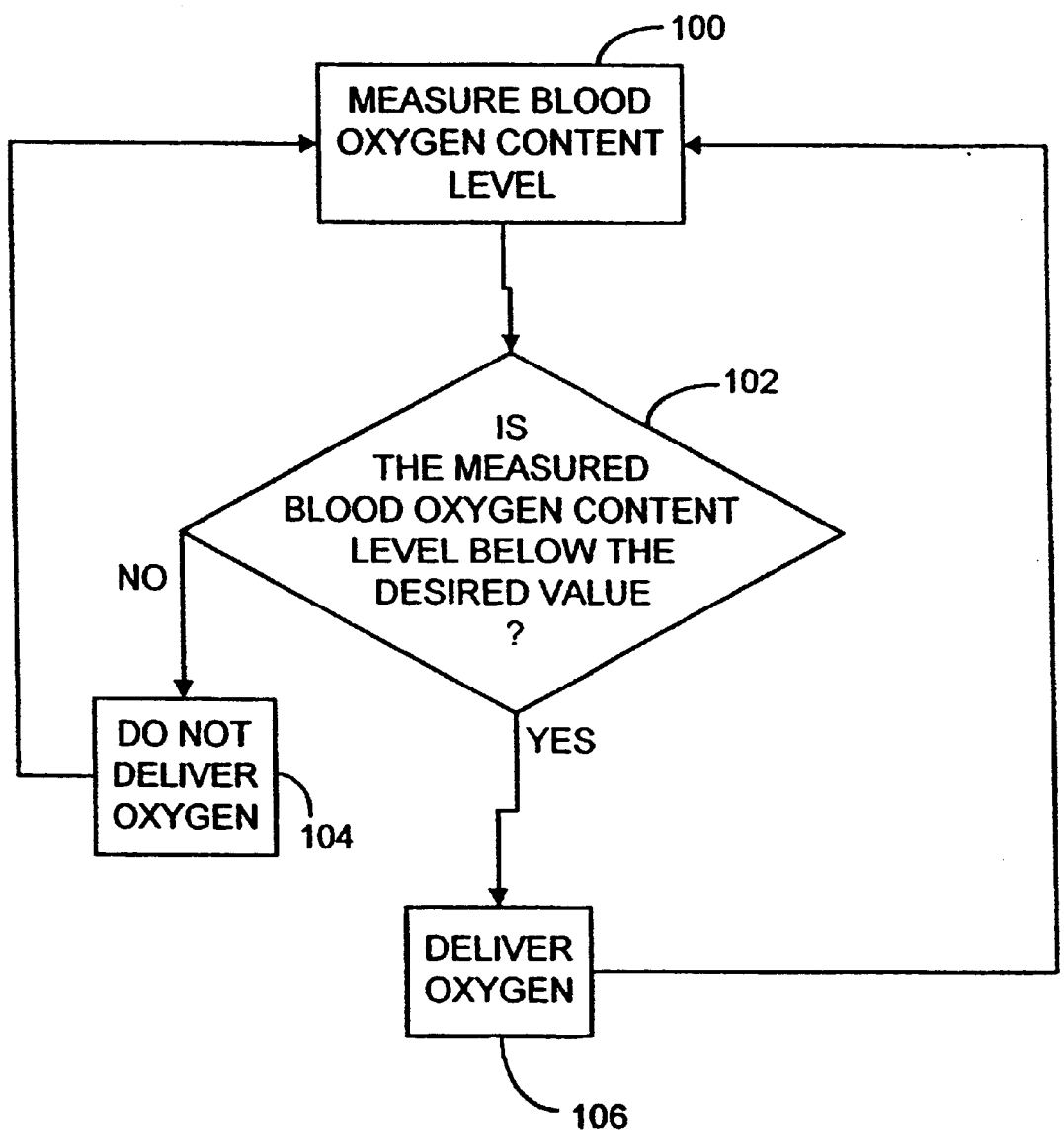
FIG. 3a is a flow diagram of one method according to the present invention.

There exist a variety of control methods that are of utility in the present method and invention. The goal of any control method is stable operation of the controlled system about a setpoint or desired value. In the preferred embodiment, the desired value is a blood oxygen saturation ($SpO_2$) of 90%. One control algorithm, the ON/OFF method, is diagrammed in FIG. 3a. This diagram assumes that the data generated by the blood oxygen content sensor is valid (validity and invalidity of that data is discussed in more detail below).

The system measures the patient's blood oxygen content level 100. With that information, a decision 102 is made. When the measured blood oxygen content level is not below the desired value no oxygen is delivered 104. When the measured blood oxygen content level is below the desired value, oxygen is delivered 106. For example, when the measured blood oxygen content level is not below the desired value, controller 10 sets a dose time of zero (D=0), thereby preventing the delivery of supplemental oxygen. Alternatively, the system may otherwise restrict the flow of oxygen by, e.g., reducing its flow to a very low value in an attempt to conserve the supplemental oxygen source. The reduction in flow can be accomplished using a variable flow valve or by introducing a flow restrictor into the system between the source 20 and the patient 16. When the measured blood oxygen content falls below the desired value, controller 10 delivers supplemental oxygen to the patient 16 by, e.g., setting a non-zero value (D>0) for the dose time or otherwise increasing the flow of oxygen to the patient.

As long as the measured blood oxygen content level remains below the desired value, the system provides oxygen when the patient is inhaling. In one relatively simple implementation, the "ON" dose time D could be very long. Preferably, however, the dose time is equal to or shorter than a typical inhalation period, in which case one or more pulses of duration D of oxygen are delivered during inhalation. This ON/OFF control approach is analogous to the operation of a furnace using a mercury switch thermostat, i.e., oxygen delivery is either ON or OFF.

Figure 3B:
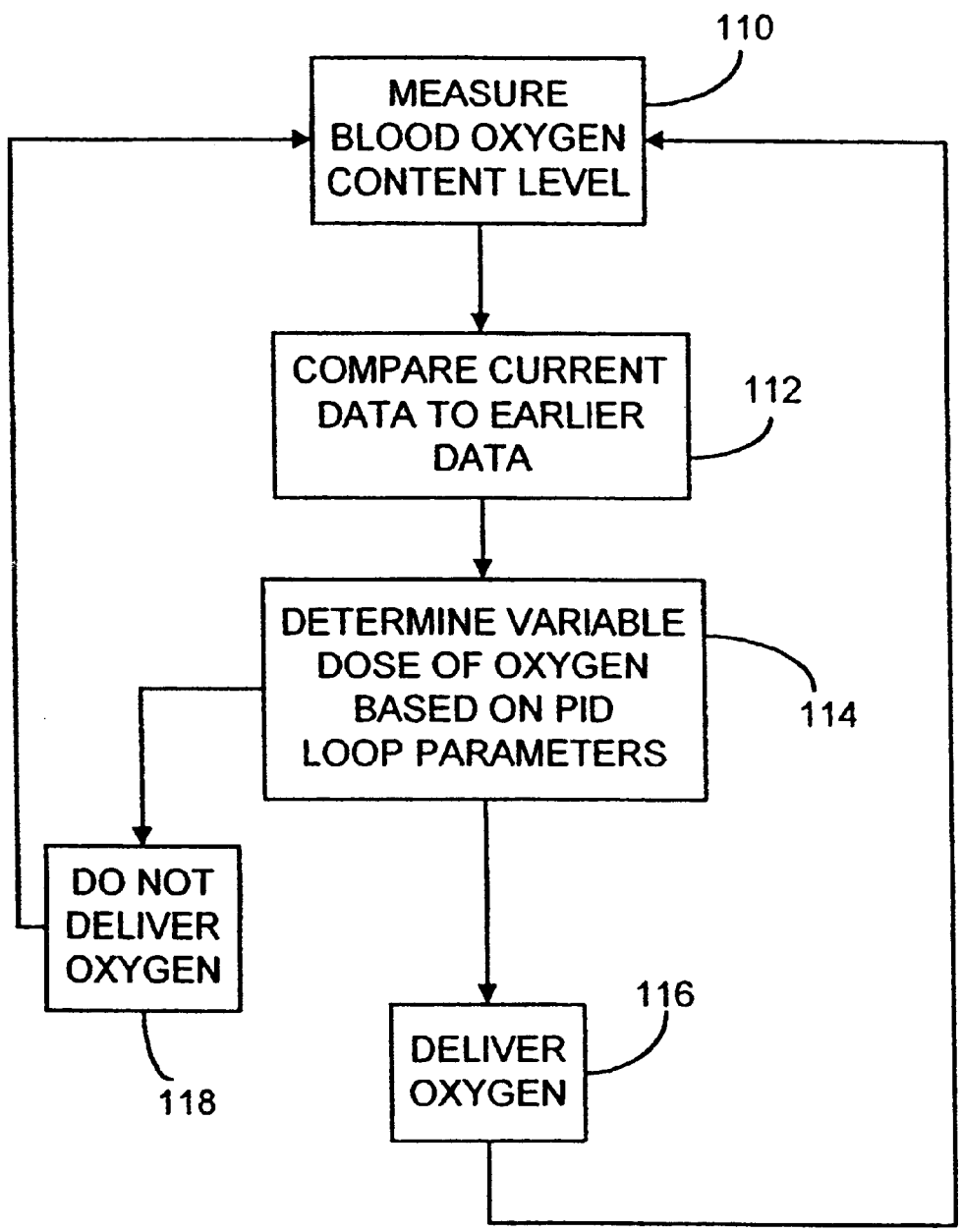
FIG. 3b is a flow diagram of another method according to the present invention.

The feedback control algorithm may alternatively use a Proportional-Integral-Derivative (PID) loop as illustrated in FIG. 3b. Other embodiments could use algorithms based on fuzzy logic, look-up tables, P or PI loops or increment/decrement methods (oxygen delivery that increases or decreases in a preprogrammed fashion relative to setpoint and/or trend). The PID algorithm is fundamentally different from the simple ON/OFF control algorithm in that it uses both the current value of the blood oxygen content and also trend information to determine whether the patient needs supplemental oxygen and, if so, how much oxygen should be delivered when the patient is inhaling. Because of the use of trend information, a system controlled with a PID loop will, at times, deliver oxygen to the patient even if their blood oxygen content is above the desired value; or, at other times, it may not deliver oxygen even if they are below the desired value. An example of when this might occur is when the patient's blood oxygen content was above the desired value, but was also dropping very quickly. In this case, the PID loop would start oxygen delivery before the blood oxygen content actually fell below the desired value. (The ON/OFF method would not start oxygen delivery until after the blood oxygen content was below the desired value). This may allow a PID control method to more effectively reduce the fluctuations of the blood oxygen content about the desired value.

A simplified flow diagram of one such PID control system is illustrated in FIG. 3b where the data stream of the measured blood oxygen content level sensor is assumed to be valid (validity/invalidity of that data is discussed in more detail below). The system measures the patient's blood oxygen content level 110. The current information is compared with earlier data 112 to determine how much oxygen (i.e., a variable dose), based on the parameters of the PID loop 114, should be delivered to the patient 116. In some instances, the parameters of the PID loop indicate that no oxygen is to be delivered 118, and in other instances some variable dose of oxygen will be delivered based on the parameters of the PID loop.

The preferred systems for implementing the methods of the present invention use a digital controller. As a result, discretization of the following continuous-time PID control equation must be performed:

$$D(t)=K_p*[e(t)+(1/T_i)*\int e(t')dt'+(T_d)*de/dt] \quad (1)$$

where $D(t)$ is the oxygen dose time at time t, $K_p$ is the loop proportional gain, $T_i$ is the integral time, $T_d$ is the derivative time, and where the integral is integrated over the range of from zero to t. The preferred embodiment utilizes a first order discretization of the continuous time PID equation. This can be seen in Equation 2, $$D(t_n)=D(t_{n-1})+A_0 e(t_n)+A_1 e(t_{n-1})+A_2 e(t_{n-2}) \quad (2)$$

where $D(t_n)$ is the control signal (oxygen dose time) generated for time period $t_n$, $e(t_n)$ is the difference between the desired level of blood oxygen saturation (the setpoint) and the measured level at time $t_{n1}$. The coefficients, $A_0$, $A_1$, and $A_2$ are given by Equations 3–5 below:

$$A_0=K_p*(1+t_n/t_i+t_d/t_n) \quad (3)$$

$$A_1=-K_p*(1+2*t_d/t_n) \quad (4)$$

$$A_2=K_p*(t_d/t_n) \quad (5)$$

where $K_p$ is the loop proportional gain, $t_i$ is the integral time, $t_d$ is the derivative time and $t_n$ is the period of the measurement (one second if using the preferred oximeter).

As mentioned, the quantity $e(t_n)$ is the difference between the $SpO_2$ value at time $t_n$ and the desired value. In one embodiment, a fixed setpoint of $SpO_2=90\%$ is used for the desired value. The control algorithm will specify doses of oxygen in order to maintain the blood oxygen saturation at this level. It is thought that this saturation level may provide the necessary correction to the patient's hypoxemia, while at the same time conserving the greatest amount of oxygen. It should be apparent to those skilled in the art that the desired value (setpoint) can be changed to achieve different therapeutic and economic goals.

Moreover, a system that uses additional physiological parameters, such as pulse rate or respiratory rate, in addition to blood oxygen content as determined by the oxygen sensor to determine a target blood oxygen level (setpoint) that changes on a rolling basis could also be implemented. For example, one may use the heart rate to monitor the patient's activity level and therefore anticipate increased or decreased need of oxygen and adjust the setpoint accordingly. Such schemes would be seeking to ameliorate the possible increased/decreased hypoxemia caused by a change in physical activity level. Such changes to the setpoint should be considered to be within the spirit and scope of the present invention.

Referring now to Equations 3–5 above, the transfer function coefficients $A_0$, $A_1$ and $A_2$ are determined by the settings of loop proportional gain $K_p$, the integral time $t_i$, the derivative time $t_d$ and the time between data points $t_n$. The determination of these values will typically be accomplished through clinical monitoring of COPD patients while the system is in use. The specific values of these loop parameters will depend on design goals such as loop stability, overshoot, time-to-achieve-control, and accuracy. Methods for obtaining values which provide for effective operation of the control loop will be known to those skilled in the art.

In one method, the control signal $D(t_n)$ is the dose time needed to maintain the blood oxygen level at the desired value. The dose time signal is provided by controller 10 to respiration sensor/valve controller 42. It is the duration of time that valve 26 will be held in the ON or open position which permits oxygen to pass from supply 20 to patient 16 (via the supplemental oxygen delivery device 18 illustrated in FIGS. 1 and 2). A dose of oxygen of duration $D(t_n)$ is provided during inhalation (as indicated by respiration sensor 40 and sensor and valve controller 42, described previously).

It should be understood that other methods besides varying the dose time could also be employed to control the patient's blood oxygen content. For example, a system which includes a variable-flow valve (as opposed to the preferred open/closed valve) could be constructed. In such a system, the controller 10 could specify the oxygen flow level. The specified flow could, in turn, be provided for a fixed period of time at the onset of each breath, or continuously. During those times in which the patient does not require supplemental oxygen and/or is not inhaling, the flow could be restricted to a low level or to zero followed by periods in which the flow is higher (when the patient is in need of supplement oxygen and is inhaling).

Alternately, the blood oxygen content could be controlled by providing a dose of oxygen on one or more sequential breaths and then delivering no oxygen on one or more subsequent breaths. In this method, the control parameter could be described as the number of breaths during which oxygen is or is not delivered. It should be understood that those skilled in the art could construct a control scheme which uses any of these alternate methods or a combination of these methods.

The controller 10 also may include a minimum limit (D min) for the dose time. If the dose time $D(t_n)$, as determined by Equation 2, is less than D min, a dose time of D min will be used instead. In one embodiment, D min will be zero. The dose time $D(t_n)$ determined by Equation 2 will, at times, be negative. This will primarily occur when the patient's blood oxygen content is greater than the desired value. Since a negative dose time is not physically meaningful, the controller will instead substitute a dose time of D min. Of course, D min could also be greater than zero.

Similarly, in one embodiment the controller 10 would also have a maximum limit (D max). If the dose time $D(t_n)$, as determined by Equation 2, is greater than D max, a dose time of D max is used instead. In one embodiment, D max is equal to twice the default dose (described in detail below). This prevents the application of excessive amounts of oxygen and thus minimizes the patient's risk of hypercapnia (carbon-dioxide retention). Those skilled in the art will appreciate that other values of D max could also be used.

In another embodiment, the controller 10 could include an "anti wind-up" provision. Because the dose time may have minimum and maximum limits (D min and D max, described above), it may be advantageous to include an anti wind-up provision to prevent the integral portion of the PID-calculated dose time from getting too large or too small. One way this could be implemented is as follows: If the previous PID-calculated dose time $D(t_{n-1})$ (from Equations 2–7) is less than D min or greater than D max, the integral term from Equation 3 is deleted (i.e., Equation 3 is replaced with Equation 3a, below):

$$A_O = K_p * (1 + t_d/t_n) \tag{3a}$$

Figure 4:
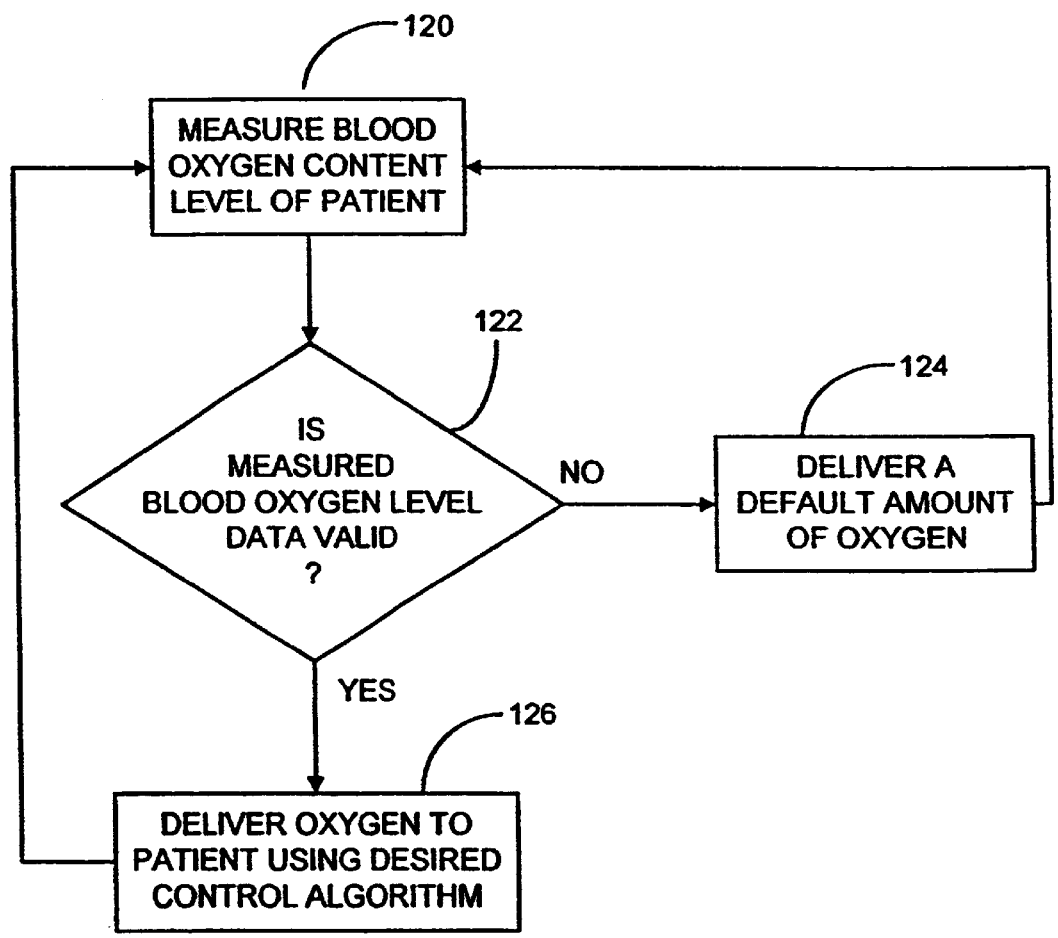
FIG. 4 is a flow diagram of one method of delivering supplemental oxygen based on whether the measured blood oxygen content data is valid or invalid.

In systems and methods according to the present invention, the ability to respond to periods of invalid or bad data in the blood oxygen content measurements is preferably provided. In the preferred methods and systems, the delivery of oxygen moves from the closed loop control described herein to open loop control based on the criteria described herein (i.e., default values, interpolated data, etc.) and back to closed loop control when the blood oxygen measurements are again valid. FIG. 4 illustrates these concepts. As shown, the system obtains a measured blood oxygen content level 120. A decision is then made as to whether the measured blood oxygen content level data is valid or invalid 122. The system may determine whether the measured blood oxygen content level data is invalid on a point-by-point basis or it may determine whether the data stream (including a plurality of data points) is invalid as discussed below. Regardless, a decision will be made as to whether the measured blood oxygen content level data is valid. If the measured blood oxygen content level data is invalid, the system will deliver a default amount of oxygen to the patient 124. If the measured blood oxygen content level data is valid, the system will deliver oxygen to the patient 126 according to the appropriate control algorithm (ON/OFF, PID loop, etc.).

In other words, the methods/systems according to the present invention will determine when the blood oxygen content data is invalid, deliver a default amount of oxygen during periods of invalid data, and then resume delivery of supplemental oxygen based on blood oxygen content when that data is again valid. The ability of the systems and methods of the present invention to move from closed to open and back to closed loop control provides a robust system that can operate with a minimum of supervision from medical personnel. Those qualities are essential in any system designed for residential or ambulatory use by sub-acute patients.

The following description illustrates some preferred methods for accomplishing these features, but it should be understood that in its essence the present invention provides for that movement from closed loop control to open loop control and back to closed loop control based on the presence of valid or invalid blood oxygen content measurements.

In one embodiment, before the measured blood oxygen saturation reading ($SpO_2$) is used for determining the dose time D of oxygen to be delivered to the patient 16 from the oxygen source 20, various error handling and artifact detection procedures are followed to prevent erroneous over- or under-dosing of oxygen to the patient. In one embodiment of the present invention, the error flags provided by the oxygen sensor 14 in the serial data stream are combined with a numerical analysis of the $SpO_2$ data to create an artifact detection and handling scheme.

The serial data stream of the preferred pulse oximeter 14 provides one data point per second. Each data point includes three bytes of information, as follows:

| | |
|---|---|
| 1st byte = Status | Bit 7 = Always set to "1" |
| | Bit 6 = Sensor disconnected, set if true |
| | Bit 5 = out of track, set if true |
| | Bit 4 = low perfusion, set if true |
| | Bit 3 = marginal perfusion, set if true |
| | Bit 2 = bad pulse, set if true |
| | Bit 1 = heart rate bit 8 |
| | Bit 0 = heart rate bit 7 |
| 2nd byte = Heart Rate | (511 = bad data) Bit "7" is always set to "0" |
| | Heart Rate Data = Bits 0–6 |
| | Plus bits 0 & 1 of status byte to provide 9 bits of resolution |
| 3rd byte = $SpO_2$ | (127 = bad data) |

The first byte of the data point may include error flags for some problems associated with pulse oximetry. These flags are examined for the occurrence of a disconnected sensor, low or marginal perfusion, out of track oximeter and bad pulse. If any of these flags are set, the accompanying $SpO_2$ and heart rate data is considered bad. If the data point is determined to be bad, a timer (Timer1) is started by the controller 10 (unless it is already running based on an earlier bad data point) which then waits for the next data point. The function of Timer1 is to track the cumulative time over which consecutive bad data points are being received. Timer1 is stopped and reset to zero each time a valid or good data point is received.

If, however, none of the flags is set, a second error check may be performed using a statistical analysis of the data. The new data point is compared to a mean value of previous data points which represents the patient's current blood oxygen content. The details of the calculation of this mean value are described below. The current data point is subtracted from the mean value to generate a difference, $\Delta SpO_2$ in %. (For the data-validity analysis below, if $\Delta SpO_2$ is less than zero, its absolute value is used.)

If the absolute value of $\Delta SpO_2 > 4\%$ and Timer1 equals zero (i.e., the last data point was valid), then the current data point is determined to be invalid. Since the time between data points in the serial data stream will be about one second, a change larger than 4 percent in the $SpO_2$ in such a short time would be physiologically impossible. If the data point is determined to be invalid using this procedure, the data is ignored, Timer1 is started and controller 10 waits for the next data point.

If, however, the absolute value of $\Delta SpO_2 > 4\%$ and Timer1 does not equal zero, then additional evaluation may be performed. The observed rate of oxygen desaturation in humans can approach 20%/minute or about 3% every 10 seconds. If Timer1 is less than 10 seconds and the absolute value of $\Delta SpO_2 > 4\%$, then the data is considered to be invalid. If Timer1 is greater than 10 seconds, but less than 20 seconds then the acceptance criteria is absolute value of $\Delta SpO_2$ less than 8% for the data to be valid. If Timer1 is greater than 20 seconds, but less than 30 seconds then the acceptance criteria is absolute value of ΔSpO₂ less than 12%. If Timer1 is greater than 30 seconds, then oxygen is delivered using the default method which is described in detail below. It should, of course, be understood that, in the above analysis, the specific values of 4%, 8%, and 12%, and the specific times of 10, 20 and 30 seconds could be replaced with different values.

Some alternate criteria for identifying when individual data points are invalid or bad could include, but are not limited to, identifying an invalid data point when: (a) the SpO₂ value is outside upper and/or lower limits (e.g., a lower limit of about 70% and/or an upper limit of about 98%); or (b) the heart rate is outside upper and/or lower limits (e.g., a lower limit of about 40 beats per minute and/or an upper limit of about 200 beats per minute).

If the data point passes all the tests, Timer1 is stopped and set to zero (if necessary) and the new mean value of blood oxygen content is calculated with the most recent data point. The new mean value is then compared to the setpoint and a dose time D is calculated as detailed above in Equations 2–5.

In one embodiment, an exponentially-weighted arithmetic mean of the previous data points is used to represent the current blood oxygen content. The new mean is calculated as follows:

$$\text{new mean} = (\text{current data point}) * W1 + (\text{previous mean}) * W2 \quad (6)$$

where $$W1 = 1 - \exp(-\Delta t/T) \quad W2 = \exp(-\Delta t/T). \quad (7)$$

Here Δt is the time between data points (one second using the preferred oximeter), and T is a parameter which represents an appropriate time scale for the averaging. If an appropriate value of T is chosen, the exponentially-weighted mean will smooth out normal point-to-point "noise" fluctuations in the pulse oximeter data without masking the real trends related to the patient's blood oxygen content. (A typical value would be T=10 seconds, although other values could be used.)

Other means could also be used to determine a mean value that is representative of the patient's current blood oxygen content. For example, a harmonic, or geometric mean might be used. (Descriptions of these types of means can be found in "Standard Mathematical Tables" by CRC Press, 24th edition, pages 470–471.) Alternately, a "running" mean might be used. In this method, the mean of a fixed, predetermined number of the most-recent data points could be used. For example, with the preferred pulse oximeter which delivers one data point per second, one could average the preceding 10 data points, thus calculating a mean which represents the patient's blood oxygen content for the previous 10 seconds.

In one embodiment, the dose time D of oxygen that is delivered to the user may depend on the validity of the data stream from the oxygen sensor. If the time over which the consecutive invalid or bad data points are received, as indicated by Timer1, exceeds a predetermined, physiologically-relevant time scale for patient desaturation (referred to as Desattime), alternative, "default" oxygen delivery procedures are employed. In one embodiment Desattime is equal to 30 seconds. The default assumption is that a patient is always in need of oxygen, unless the blood oxygen content sensor positively indicates that they are not.

If the current oxygen sensor data point is invalid, but Timer1 is less than Desattime, the oxygen dose time D may remain unchanged from its current value. The system will provide a dose of this duration at the onset of inhalation. The process of gathering and evaluating blood oxygen saturation data then continues. Prior to the onset of invalid data, the system was either administering oxygen to correct a deficiency or the patient was in no need of oxygen. Thus, in this embodiment it is assumed that the patient's oxygen needs have not changed during this short time of invalid data and the status quo is maintained. If the patient was receiving no oxygen prior to the invalid data (e.g., dose time D=0), the system will not administer any oxygen. If, however, the patient was receiving oxygen (e.g., D>0), the system will typically continue to administer the same dose by responding to inhalation as described above. This will preferably continue until either a valid data point is received and a reevaluation can be made of the patient's condition or Timer1 exceeds Desattime.

If the oxygen sensor data points continue to be invalid and Timer1 exceeds Desattime, then the device will default to another oxygen delivery method. In the default method, the controller 10 will default to administering a prescription-equivalent dose of oxygen to the patient 16 from the oxygen source 20 via the demand delivery module 12. This default dose of oxygen could take many forms: In one embodiment, the default could be a continuous flow of oxygen. To implement this, the system could output a very large dose time to hold valve 26 in the ON position which allows oxygen to flow from source 20 to patient 16. Alternately, in the preferred embodiment, the default mode would provide a short dose of oxygen (of duration D=Ddefault) at the onset of inhalation for almost every breath. In this preferred embodiment, Ddefault would be shorter than a typical inhalation period, in which case the system would provide pulses of duration Ddefault synchronized with each inhalation (demand mode). This will continue until such time as the blood oxygen content data is valid and closed-loop control over oxygen delivery can start anew.

It is possible to envision additional alternate methods of default flow. In one such alternate embodiment, the valve does not necessarily open with each and every breath. It should be understood that these alternate methods of implementing a default flow still fall within the scope of the present invention. The object of the default method is to provide a total flow of oxygen during this period of default operation that is no less than the physiological equivalent amount that is prescribed to the patient by the physician. (Physiological equivalence meaning the amount dispensed by other demand delivery devices to provide adequate oxygen therapy.) It should be understood that the notion of physiological equivalence as regards demand delivery devices will change over time as their effects on the physiology of COPD patients is better understood by the medical community. Current practice indicates that 35 ml delivered every other breath at the beginning of inhalation is equivalent to a continuous flow of 2 liters/minute of pure oxygen.

In one embodiment of the invention, the duration of the default dose (Ddefault) may be set by the patient's respiratory therapist using a hardware switch on the user interface 32 that is not accessible to the patient. Other techniques of setting the pulse width may be possible, such as a remote controllers, push buttons, etc.

Also, in one embodiment, if Timer1 exceeds Desattime, then the previous mean value of the blood oxygen saturation is reset and data acquisition starts anew. In this way, it is assumed that the old SpO₂ information is no longer valid for the patient's current physical state and that to properly administer oxygen a more current measure of the blood oxygen level is needed. Thus, by using Timer1, a period of invalid data that exceeds Desattime will always lead to the administration of oxygen to the patient. This will correct any undetected desaturation events. Moreover, the controller 10 will always use the most current, valid information regarding the patient's blood oxygen level.

It should also be understood that other methods for recognizing and handling erroneous data points from the oxygen sensor could be devised. Those skilled in the art could create different algorithms for handling invalid data points, such as replacement of invalid data points with interpolated values based on the recent trend in the blood oxygen saturation. Alternative methods of identifying and rejecting invalid data points should be considered to be within the scope of the present method and system.

Another method for determining whether the oxygen sensor data is valid or invalid can be based on the data stream (a plurality of data points) rather than the individual data points. For example, instead of tracking the time since the most recent valid data point or points, the system could instead determine if the data stream is valid or invalid by comparing the number of valid data points in a "look-back" window (for example, the 60 to 100 most recent data points) to a preset minimum threshold. If the number of valid data points in the look-back period is greater than or equal to the specified minimum, the data stream is considered to be valid and the calculated dose is delivered; if the number of valid data points is less than the minimum, the default dose is delivered.

Those skilled in the art will understand that a wide range of possibilities for oxygen delivery in default mode beyond those that have been described here could be used. Although they are not described in detail herein, they should be considered as falling within the scope of the methods according to the present invention.

If invalid data is a problem, the controller 10 may be used to notify the patient of a problem with the pulse oximetry via the user interface 32 and/or alarm 38. This notification may take the form of a warning light, readout, buzzer or some combination of these. Those skilled in the art may also conceive of other methods of warning the user that are not detailed herein. After the warnings have been issued and default demand flow mode entered, the controller 10 resumes monitoring the output of the oxygen sensor for valid data.

Along with monitoring the breathing cycle for oxygen delivery, the invention makes provision for the detection of apnea, the cessation of breathing for a prolonged period of time. Timer2 starts each time an inhalation is detected. If the elapsed time between breaths is greater than a predetermined time, e.g., 15 seconds, as determined by Timer2, then the alarm circuit 38 is activated by the controller 10 to signal the patient of a possible apneic event. These alarms preferably stop sounding upon detection of the next inhalation.

Other alarms and indicators that can be included in the systems and methods of the present invention include hypoxia alarms, high respiration rate alarms, high/low pulse rate alarms, and patient monitoring indicators. These alarms and/or indicators can be used to warn the patient that their supplemental oxygen equipment is not operating properly, they are not using it properly, or they are having other problems and need to seek medical treatment.

In the case of an hypoxia alarm, the patient could be provided with a visible and/or audible alert when their blood oxygen saturation level has been below a healthy level for a period of time—even though they have been using the above-described device. This condition could be caused, e.g., by a malfunctioning of the supplemental oxygen equipment or a worsening of the patient's respiratory condition. In normal operation of the preferred embodiment as described above, the device would increase the dose time D(t) in response to the patient's hypoxia, up to a preset upper-limit dose time D max. It is possible that the patient's condition could have worsened so much so that even this maximum dose is not sufficient to keep their blood oxygen saturation at a healthy level. It would be advantageous to alert the patient to this condition so they may seek appropriate medical attention. This could enable earlier detection and treatment of potentially dangerous and costly health conditions.

The hypoxia alarm could be implemented in software, hardware, or in a combination of software and hardware. In the methods described above, the controller 10 may already calculate a mean value of blood oxygen content from the valid blood oxygen saturation data points. In the preferred embodiment, the mean value that is already calculated is an exponentially-weighted arithmetic mean with a typical time constant T=10 seconds. This mean represents the average blood oxygen saturation for the previous 10 seconds. For the hypoxia alarm, a second mean value of blood oxygen saturation, for a longer period (e.g.. T=1 hour) could be calculated in an analogous manner. In the preferred embodiment, this hypoxia alarm mean would also be an exponentially-weighted mean because it eliminates the need to store each of the many data points that would be collected over the longer period, thereby decreasing the memory requirements.

It should be understood, however, that other methods of calculating a mean as discussed above could also be used. When the second mean falls below a preset limit representing the lower limit for healthy blood oxygen levels (e.g., 88%), controller 10 could alert the patient via alarm circuit 38. In the preferred embodiment, the time period for the second mean is 1 hour, and the lower limit for blood oxygen saturation is 88%; however, it should be clear that other values could be used for these parameters.

In the case of a high respiration rate alarm, the patient could be provided with a visible and/or audible alert when their respiration rate has been above a healthy level for a period of time. Some patients with respiratory diseases will compensate for an impaired respiratory system by maintaining a higher than normal breathing rate. These patients can sometimes maintain a healthy blood oxygen saturation, but over the long term, the increased respiration rate is also detrimental to their health. The onset of a period of increased respiration rate could be caused by a malfunctioning of the supplemental oxygen equipment or a worsening of the patient's respiratory condition.

In normal operation of the preferred embodiment as described above, the device increases the dose time D(t) in response to the patient's hypoxia. It is possible that the patient's condition could have worsened, but the patient is compensating by breathing at a higher rate. As with hypoxia, it would be advantageous to alert the patient to this condition so they may seek appropriate medical attention.

This alarm could be implemented in software, hardware, or in a combination of software and hardware. The system described above already measures the elapsed time between each breath via Timer2. For the high-respiration rate alarm, a mean value of the elapsed time between each breath could be calculated in a manner analogous to the mean blood oxygen levels. In the preferred embodiment, this mean would also be an exponentially-weighted mean. It should be understood, however, that other methods of calculating a mean as described above could also be used. When the mean elapsed time between breaths falls below a preset limit corresponding to the upper limit for healthy respiration rates (e.g., minimum elapsed time of two seconds, corresponding to a breathing rate of 30 breaths per minute), the system could alert the patient via controller 10 and alarm circuit 38. In the preferred embodiment, the time period for calculating the mean is 1 hour, and the lower limit for elapsed time between breaths is 2 seconds (30 breaths per minute); however, it should be clear that other values could be used for these parameters.

In the case of a high/low pulse rate alarm, a visible and/or audible alert could be provided to the patient when their pulse rate has been above or below healthy levels for a period of time. Excessively high or low pulse rates could be an important indication that the patient needs medical treatment. It would be advantageous to alert the patient to these conditions so they may seek appropriate medical attention.

In the preferred embodiment, these alarms would be implemented in software, hardware, or in a combination of software and hardware. The preferred oxygen sensor typically provides pulse rate data (in addition to blood oxygen data). A mean pulse rate could be calculated in a manner analogous to the calculation of other means, described above. As with the other alarms, in the preferred embodiment, this mean would also be an exponentially-weighted mean or, alternatively, other means or averages could be used.

When the mean pulse rate falls above or below preset limits (e.g., less than 40 or above 180 beats per minute), the system could alert the patient via alarm circuit 38. In the preferred embodiment, the time period for the mean is 20 minutes, the lower limit for pulse rate is 40 beats per minute, and the upper limit for pulse rate is 180 beats per minute; however, it should be clear that other values could be used for these parameters.

Among the indicators that could be provided include various patient and equipment monitoring functions. In the preferred embodiment, these indicators could be implemented in software, hardware, or in a combination of software and hardware. The information provided by these indicators could be useful to the patients, respiratory therapists, physicians, etc. Some examples of indicators are described below.

One indicator that could be useful is an "ON-time" indicator. An important factor in treating patients that require supplemental oxygen is monitoring their compliance with their oxygen prescription. Some patients will not use their oxygen equipment as much as they should. Medical studies have shown that most patients must use their supplemental oxygen equipment at least 18 hours per day in order to receive significant benefits from it. The ON-time parameter would indicate the total amount of time that the device has been powered ON (analogous to the "hour meter" found on most oxygen concentrators), thus giving an indication of the total time the equipment was used since the ON-time parameter was last reset to zero. In the preferred embodiment, a timer would be started by controller 10 each time the unit was turned ON. When timer reached a value of, e.g., one minute, controller 10 would increment a non-volatile memory location and reset and restart the timer. In this manner, a memory location associated with the ON-time timer would count the number of minutes the apparatus had been powered ON. The memory location associated with the ON-time timer would preferably be non-volatile and, as a result, the total minute count would be retained while the unit was powered OFF. When powered ON again, counting would resume from the previously accumulated value. In the preferred embodiment, the ON-time timer could be accessed and reset via the user interface 32.

It may also be useful to track the total number of times each alarm condition has occurred. In the preferred embodiment, a separate non-volatile memory location would be used to count the number of times each alarm condition had occurred. Each time an alarm condition occurred, the associated memory location would be incremented. In addition to the three alarms described above, the preferred embodiment could also count the number of apnea alarms. The various alarm-count parameters could be accessed and reset, e.g., via the user interface 32.

It may also be useful to keep track of the total amount of time the unit was in "default" mode as described above. In a manner similar to tracking ON-time, the default time monitor would preferably consist of a non-volatile memory location that would be incremented each time the timer reached one minute and the unit was in the default mode. In a similar manner, a feedback-control-time parameter could be calculated (although this parameter may be more easily obtained by subtracting the default time from the ON-time). As with the other monitored parameters, default time would preferably be accessed and reset via the user interface 32.

It may also be useful to keep track of the total number of times the apparatus entered the "default" mode. In the preferred embodiment, a separate non-volatile memory location would be used to count the number of times the default delivery condition had occurred. Each time the apparatus entered the default delivery mode, the associated memory location would be incremented. The default count parameter would preferably be accessed and reset via the user interface 32.

It may also be useful to keep track of the total amount of time the patient was hypoxic (e.g., $SpO_2 < 88\%$). In a manner similar to tracking the ON-time, the hypoxic-time monitor would consist of a non-volatile memory location that would be incremented each time the timer reached one minute and the patient was hypoxic (and the $SpO_2$ data was deemed valid). As with the other monitored parameters, hypoxic-time could be accessed and reset via the user interface 32.

It may also be useful to keep track of the average duration of the pulses of oxygen that are provided at each inhalation (i.e., the average dose time). The average-dose-time parameter could provide a useful indication of the amount of supplemental oxygen that was required to keep the patient's blood properly oxygenated. Trends in this parameter could be useful for tracking the overall efficiency of the patient's respiratory condition. For example, a measurable increase in the average-dose-time (i.e., an increase in the amount of supplemental oxygen needed) could indicated a worsening of the patient's condition, and thus provide an early warning allowing the patient to seek medical attention before their condition required a costly hospitalization.

In the preferred embodiment, two nonvolatile memory locations would be used to calculate average-dose-time: a counter and an accumulator. Each time, e.g., an inhalation was sensed, the current dose time (as indicated by controller 10) would be added to accumulator and the counter would be incremented. The average-dose-time could then be calculated by dividing the accumulator value by the counter value. As with the other monitored parameters, average-dose-time could be accessed and reset via the user interface 32.

In addition to those parameters specifically recited herein, other useful parameters may also be generated. For example, average $SpO_2$ (the patient's average blood oxygen saturation); average respiration rate; average heart rate; etc.

Monitoring of these parameters could also be implemented in software, hardware, or in a combination of software and hardware.

Various methods and systems for conserving supplemental oxygen delivery to a sub-acute patient based on continuous blood oxygen content measurements and inhalation have been described above. Many changes, alterations and variations of the subject invention will become apparent to those skilled in the art after consideration of this specification and the accompanying figures and diagrams of the preferred embodiments. For example, the values chosen for, e.g., $\Delta SpO_2$, Timer1, Timer2, etc., are intended to be exemplary of some preferred values and should not limit the scope of the invention unless the values are explicitly recited in the claims. All such changes, modifications, variations, etc. are deemed to be covered by the claims which follow.

What is claimed is:

1. A method of controlling supplemental oxygen delivery for sub-acute care comprising:
   continuously measuring blood oxygen content of a patient to obtain a measured blood oxygen content level;
   delivering a variable dose of supplemental oxygen from an oxygen source to the patient when the patient is inhaling, wherein the variable dose is at least partially determined based on the measured blood oxygen content level.

2. A method according to claim 1, wherein the variable dose of supplemental oxygen is at least partially based on a difference between a desired value for the measured blood oxygen content and the measured blood oxygen content.

3. A method according to claim 2, wherein the desired value for the measured blood oxygen content level is about 90%.

4. A method according to claim 1, wherein the variable dose of supplemental oxygen is at least partially based on a trend in measured blood oxygen content as measured at different times.

5. A method according to claim 1, wherein the variable dose includes a zero dose.

6. A method according to claim 1, wherein the supplemental oxygen is delivered through a supplemental oxygen delivery device.

7. A method according to claim 6, wherein the supplemental oxygen delivery device comprises a nasal cannula.

8. A method according to claim 1, further comprising sensing variations in respiration of the patient to determine when the patient is inhaling.

9. A method according to claim 8, wherein the sensing comprises sensing when the patient is inhaling.

10. A method according to claim 8, wherein the sensing is performed using a flow sensor.

11. A method according to claim 10, wherein the flow sensor comprises a bidirectional flow sensor.

12. A method according to claim 1, wherein the method is performed in a residential setting.

13. A method according to claim 1, wherein the measured blood oxygen content level is obtained using a pulse oximeter.

14. A method according to claim 1, further comprising:
   determining if the measured blood oxygen content level is invalid; and
   delivering a default amount of supplemental oxygen to the patient when the measured blood oxygen content level is invalid.

15. A method according to claim 1, further comprising:
   determining if the measured blood oxygen content level is invalid; and
   replacing the invalid measured blood oxygen content level with a value based on recent trend in blood oxygen content.

16. A method according to claim 1, wherein the variable dose of supplemental oxygen is at least partially based on a difference between a desired value for the measured blood oxygen content and the measured blood oxygen content, and wherein the method further comprises changing the desired value for the measured blood oxygen content level.

17. A method according to claim 16, wherein changing the desired value for the measured blood oxygen content level comprises monitoring the patient's heart rate and changing the desired value for the measured blood oxygen content level in response to change in the patient's heart rate.

18. A method of controlling supplemental oxygen delivery for sub-acute care comprising:
   continuously measuring blood oxygen content of a patient to obtain a measured blood oxygen content level;
   sensing variations in respiration of the patient to determine when the patient is inhaling;
   delivering a variable dose of supplemental oxygen from an oxygen source to the patient through a supplemental oxygen delivery device when the patient is inhaling, wherein the variable dose of supplemental oxygen is at least partially based on a difference between a desired value for the measured blood oxygen content level and the measured blood oxygen content level.

19. A method according to claim 18, wherein the variable dose of supplemental oxygen is at least partially based on a trend in measured blood oxygen content level as measured at different times.

20. A method according to claim 18, wherein the variable dose includes a zero dose.

21. A method according to claim 18, wherein the measured blood oxygen content level is obtained using a pulse oximeter and further wherein the method comprises:
   determining if the blood oxygen content level obtained by the pulse oximeter is invalid;
   delivering a default amount of supplemental oxygen to the patient when the measured blood oxygen content level is invalid.

* * * * *